(12) United States Patent
Andrysek

(10) Patent No.: US 7,909,885 B2
(45) Date of Patent: Mar. 22, 2011

(54) SWING-PHASE CONTROLLER WITH AN ARTIFICIAL JOINT

(76) Inventor: Jan Andrysek, Toronto (CA)

( * ) Notice: Subject to any disclaimer, the term of this patent is extended or adjusted under 35 U.S.C. 154(b) by 0 days.

(21) Appl. No.: 11/989,192

(22) PCT Filed: Jul. 21, 2006

(86) PCT No.: PCT/CA2006/001181
§ 371 (c)(1),
(2), (4) Date: Jan. 22, 2008

(87) PCT Pub. No.: WO2007/009240
PCT Pub. Date: Jan. 25, 2007

(65) Prior Publication Data
US 2009/0088867 A1 Apr. 2, 2009

Related U.S. Application Data

(60) Provisional application No. 60/701,487, filed on Jul. 22, 2005.

(51) Int. Cl.
*A61F 2/64* (2006.01)
*A61F 2/68* (2006.01)

(52) U.S. Cl. .......................................................... 623/43
(58) Field of Classification Search ............... 623/39–46
See application file for complete search history.

(56) References Cited

U.S. PATENT DOCUMENTS

| | | | |
|---|---|---|---|
| 5,133,773 A | 7/1992 | Sawamura et al. | |
| 5,376,137 A * | 12/1994 | Shorter et al. | 623/44 |
| 5,904,721 A | 5/1999 | Henry et al. | |
| 6,652,585 B2 | 11/2003 | Lange | |
| 6,658,540 B1 | 12/2003 | Sicola et al. | |
| 7,044,983 B1 | 5/2006 | Cheng | |
| 2005/0015156 A1 | 1/2005 | Hikichi | |
| 2005/0027370 A1* | 2/2005 | Chen et al. | 623/26 |

* cited by examiner

*Primary Examiner* — Bruce E Snow
(74) *Attorney, Agent, or Firm* — Pillsbury Winthrop Shaw Pittman LLP

(57) ABSTRACT

An artificial joint including a stance-phase control means having a flexing axis and a control axis and a swing-phase control means adapted to engage the stance-phase control means. The perpendicular distance between the flexing axis and the swing-phase control means and the perpendicular distance between the control axis and the swing-phase control means are equal when the artificial joint rotates about the flexing axis up to 65°.

8 Claims, 11 Drawing Sheets

SWING-PHASE CONTROLLER WITH AN ARTIFICIAL JOINT

This application claims the benefit of PCT/CA2006/001181 filed Jul. 21, 2006, which claims the benefit of U.S. Provisional Application No. 60/701,487 filed Jul. 22, 2005.

FIELD OF THE INVENTION

This invention relates in general to a mechanism for controlling a joint's movement and more particularly to an artificial joint with a swing-phase controller.

BACKGROUND OF THE INVENTION

Artificial joints generally require mechanisms to control their movement. For example an artificial knee joint or prosthetic joint will be prescribed for a person with a through-knee (TK) or an above-knee (AK) amputation, i.e. a person without a knee joint, shank or foot. The ability for the knee to bend or articulate during sitting, kneeling or ambulating is desirable. It is also desirable to have the ability to control the leg during the swing-phase of the gait when the person is walking or running. By improving control you also improve the look of the gait and make the gait look more natural. Finally the joint has to provide sufficient support to the person.

When standing or putting weight on the leg, as during the support-phase or stance-phase of the gait cycle it is undesirable for the artificial joint to bend uncontrollably as this will cause the amputee to fall. This is referred to as "stance-phase control". Amputees have some control during stance by the way they load the leg and how they use their remaining muscles at the hip. Alternatively, a prosthetist can align a prosthesis to be more or less stable by placing the knee joint axis behind the load bearing plane or load line. However, this tends not to produce ideal gait characteristics. While many different designs have been proposed, the majority of prosthetic knee joints are designed to address the issue of stance-phase control, i.e. keeping the knee from articulating when the prosthesis is supposed to be providing support. A prosthetic knee joint may have a built-in "locking" mechanism for this purpose.

The "swing-phase control" refers to the control of the joint's movement or articulation during the swing phase of the gait cycle to make the gait more efficient and more natural looking. Traditionally pneumatics or hydraulics are used in prosthetics to help control the swing-phase, as they are velocity dependent. Therefore as the gait velocity changes, the knee resistance changes. This is a beneficial attribute, because greater resistance is needed at higher velocities to provide adequate control of the joint. For example during walking, the air in a first chamber of a cylinder of a traditional pneumatic mechanism begins to compress as the knee begins to bend at the beginning of the swing-phase. Some of the air is displaced into a second chamber on the opposing side of the cylinder. A valve is used to control the flow rate and therefore the resistance. However the compression of the air in the first chamber also acts like a spring. The damping resistance and compressed air spring force act to slow the progression of knee flexion until the knee begins to extend. This acts to bring the leg forward quicker and limits the amount of heel-rise to normal levels. As the leg is extending, the air in the second chamber now compresses and before the knee fully extends, acts as a cushion (in the same manner as before) to slow the knee extension. This prevents the leg from slamming into the extended position (referred to as terminal impact). A hydraulic mechanism works in a similar manner but does not provide a spring force as the fluid is incompressible.

Prior art artificial joints have addressed some of the noted issues for both stance and swing-phase control. For example, many knees utilize hydraulic mechanisms to provide stance/swing-phase control including those described in U.S. Pat. Nos. 5,376,137, 6,658,540 B1 and 6,652,585 B2. These devices address how the hydraulic mechanism is controlled to provide very high resistance to flexion during stance, and lower resistances to flexion and extension during swing. However the prior art does not address a swing-phase controller that efficiently functions within an artificial joint having a dual axis (knee flexion axis and control axis) stance-phase controller.

Thus a swing-phase controller with an artificial joint which controls the swing-phase of the joint through a large range of motion, is light weight, compact, low cost, produces more efficient and natural looking gait, can be used in other applications such as orthotic and robotic, decreases wear on other components in the artificial joint, and does not interfere with the stance-phase mechanism of the artificial joint is desirable.

SUMMARY OF THE INVENTION

An object of one aspect of the present invention is to provide an improved swing-phase controller for an artificial joint in combination with a dual axis stance-phase controller.

In accordance with one aspect of the present invention there is provided an artificial joint including a stance-phase control means having a flexing axis and a control axis and a swing-phase control means adapted to engage the stance-phase control means. This engagement results in the perpendicular distance between the flexing axis and the swing-phase control means and the perpendicular distance between the control axis and the swing-phase control means being relatively equal when the artificial joint articulates about the flexing axis up to 65°.

Conveniently, the swing-phase control means includes a piston and cylinder assembly that has a first end adapted to engage an upper coupling element of the stance-phase control means, and a second end adapted to engage a lower coupling element of the stance-phase control means.

Preferably, the piston and cylinder assembly has a piston linkage assembly at the first end of the stance-phase control means so that the perpendicular distance from the piston linkage assembly to the flexing axis and the perpendicular distance from the piston linkage assembly and the control axis are relatively equal when the artificial joint articulates about the flexing axis up to 65°.

In accordance with another aspect of the present invention there is provided a swing-phase controller for an artificial joint having a flexing axis, a control axis, an upper coupling element, and a lower coupling element, where the swing-phase controller includes a piston assembly having a first end and a second end. The first end is adapted to engage the upper coupling element wherein the perpendicular distance from the piston assembly to the flexing axis and the perpendicular distance from the piston assembly and the control axis are relatively equal when the artificial joint articulates about the flexing axis up to 65°. The swing-phase controller further includes a cylinder assembly having a first end and a second end. The second end is adapted to engage the lower coupling element so that the second end of the piston assembly is adapted to engage the first end of the cylinder assembly.

Conveniently both the artificial joint with the stance-phase controller and the swing-phase controller, and the swing-phase controller on its own may be either hydraulic or pneumatic assemblies and applied to prosthetic, orthotic or robotic applications.

Advantages of the present invention are an artificial joint that can control the swing-phase of the joint through a large range of motion up to 65°, is light-weight, compact, low cost, provides for a more efficient and natural looking gait for the user, can be used in a variety applications such as prosthetic, orthotic and robotic, eliminates or decreases wear on the locking mechanism and the upper coupling element of the artificial joint as it does not interfere with these mechanisms, eliminates or reduces improper engagement of other components in the joint, and provides improved support which reduces a wobbly effect.

BRIEF DESCRIPTION OF THE DRAWINGS

A detailed description of the preferred embodiments is provided herein below by way of example only and with reference to the following drawings, in which.

Figure 1:
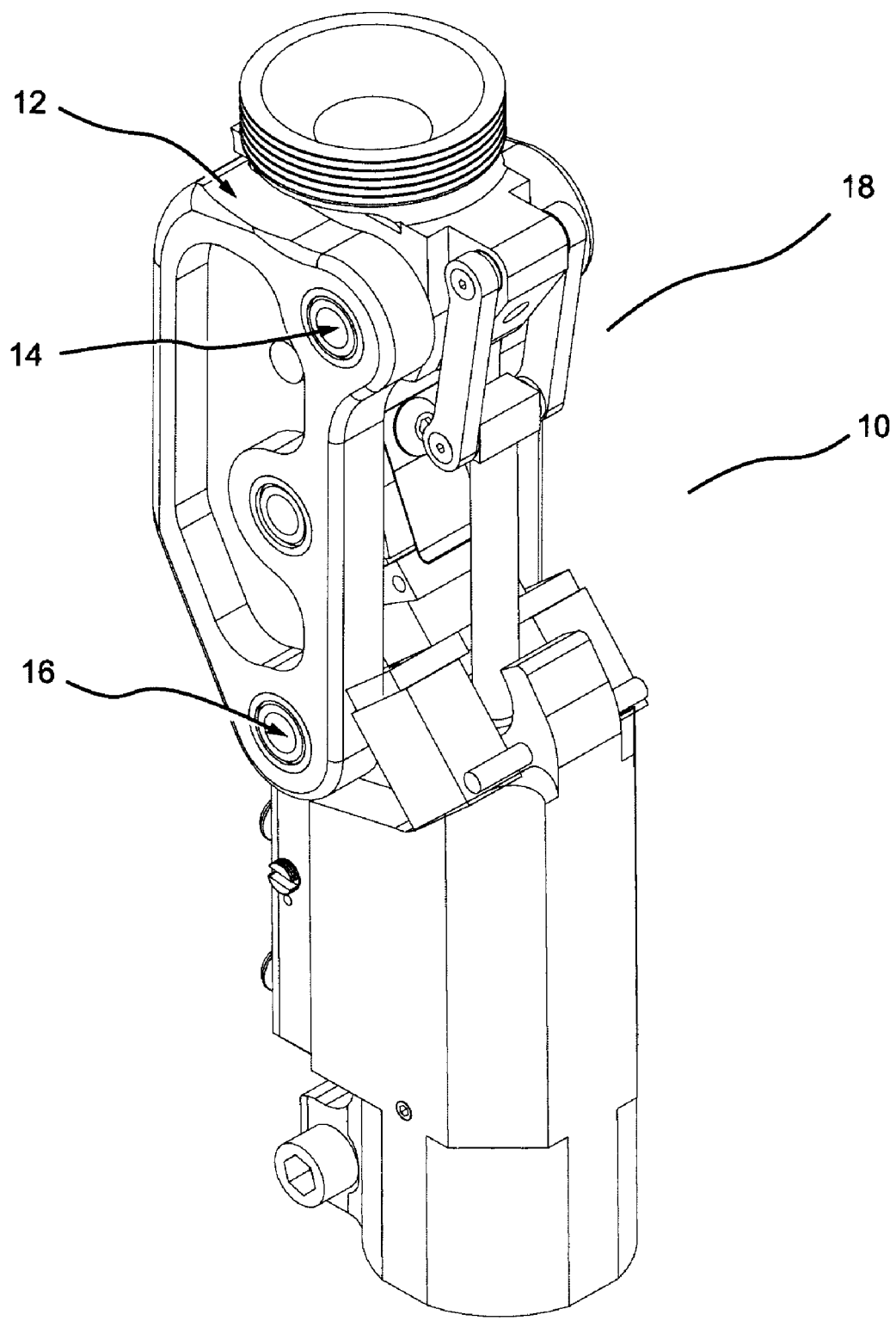
FIG. 1 in a perspective view, illustrates an artificial joint in accordance with a preferred embodiment of the present invention.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 2:
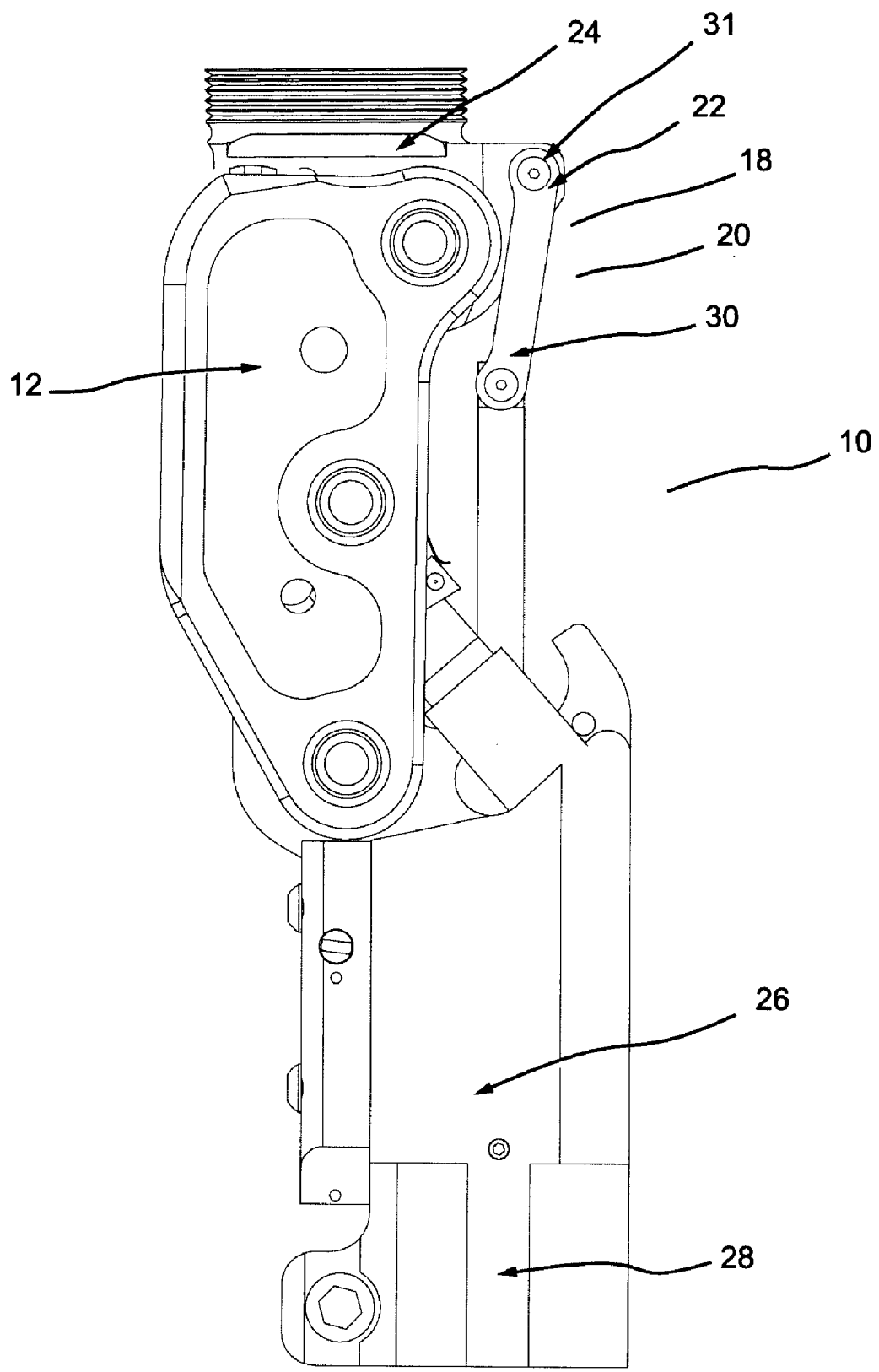
FIG. 2 in a side view, illustrates the artificial joint of FIG. 1.

Referring to FIGS. 1 and 2, there is illustrated in perspective and side views, an artificial joint 10 in accordance with a preferred embodiment of the present invention. The artificial joint 10 includes a stance-phase control means 12 having a flexing axis 14 and a control axis 16 and a swing-phase control means 18 adapted to engage the stance-phase control means 12. The perpendicular distance between the flexing axis 14 and the swing-phase control means 18 and the perpendicular distance between the control axis 16 and the swing-phase control means 18 are relatively equal when the artificial joint 10 articulates about the flexing axis 14 up to 65°.

Figure 5:
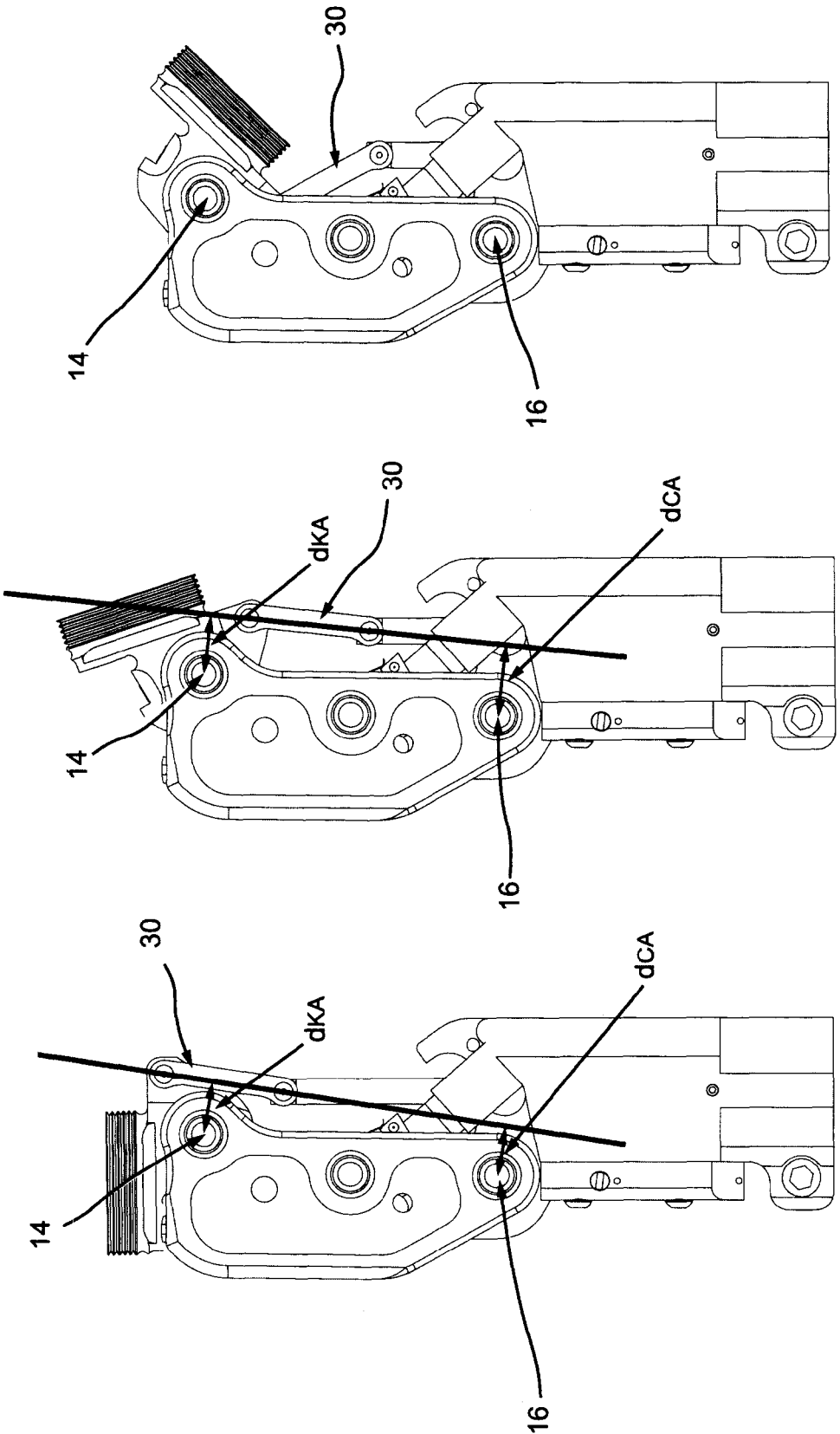
FIGS. 5a, b and c in side views, illustrate the artificial joint of FIG. 1 and the perpendicular distance between the piston linkage and both the flexing axis and the control axis.

The swing-phase control means 18 further includes a piston and cylinder assembly 20 that is adapted to engage the stance-phase control means 12. The piston and cylinder assembly 20 has a first end 22 that is adapted to engage an upper coupling element 24 of the stance-phase control means 12, and a second end 26 adapted to engage a lower coupling element 28 of the stance-phase control means 12. The piston and cylinder assembly 20 is further defined as having a piston linkage assembly 30 having a first end 31 mounted to the upper coupling element 24. As illustrated in FIGS. 5a-c, the perpendicular distance therefore from the piston linkage assembly 30 to the flexing axis 14 and the perpendicular distance from the piston linkage assembly 30 and the control axis 16 are relatively equal when the artificial joint 10 rotates about the flexing axis 14 up to 65°.

Figure 3:
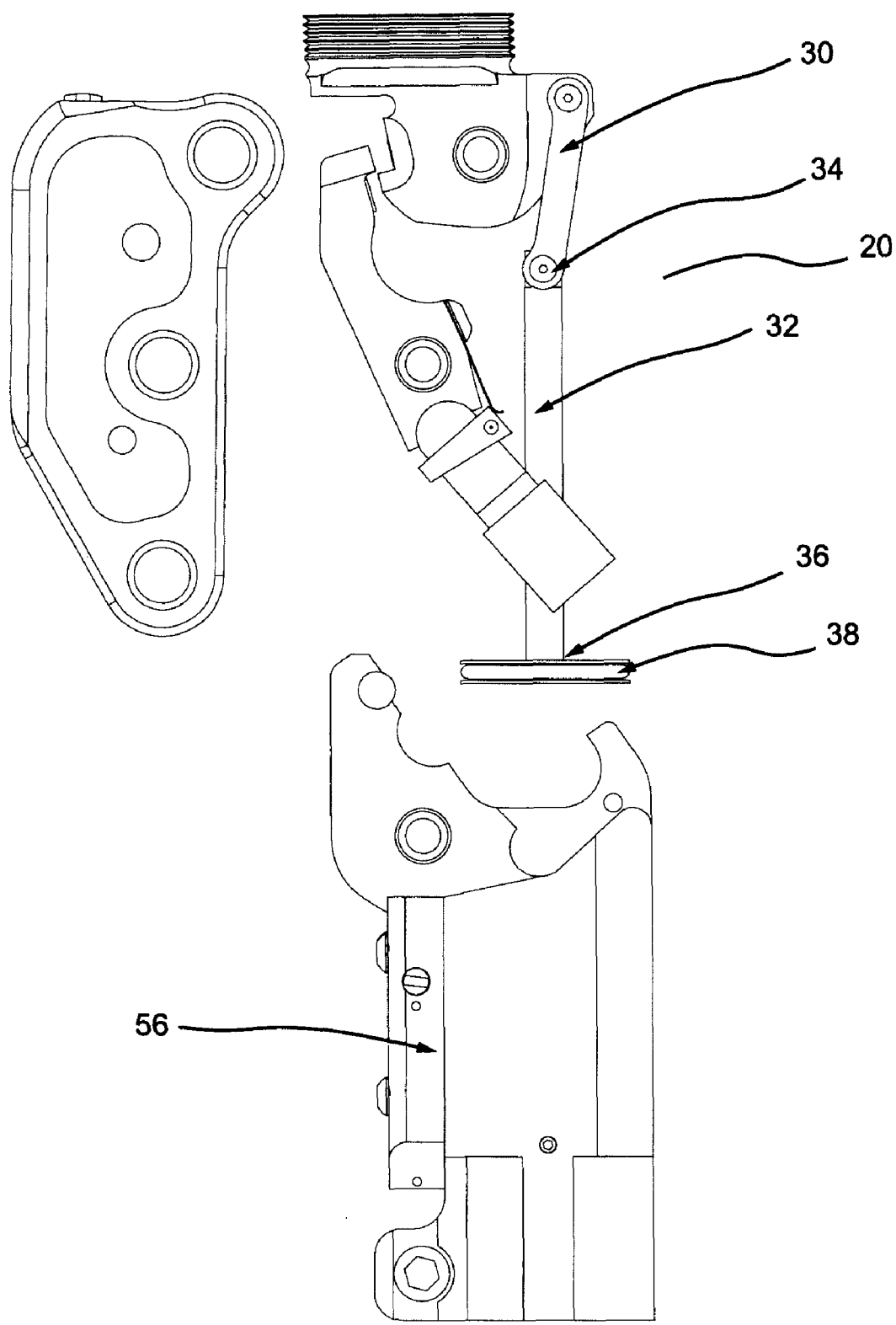
FIG. 3 in an exploded view, illustrates the artificial joint of FIG. 1.
Figure 4:
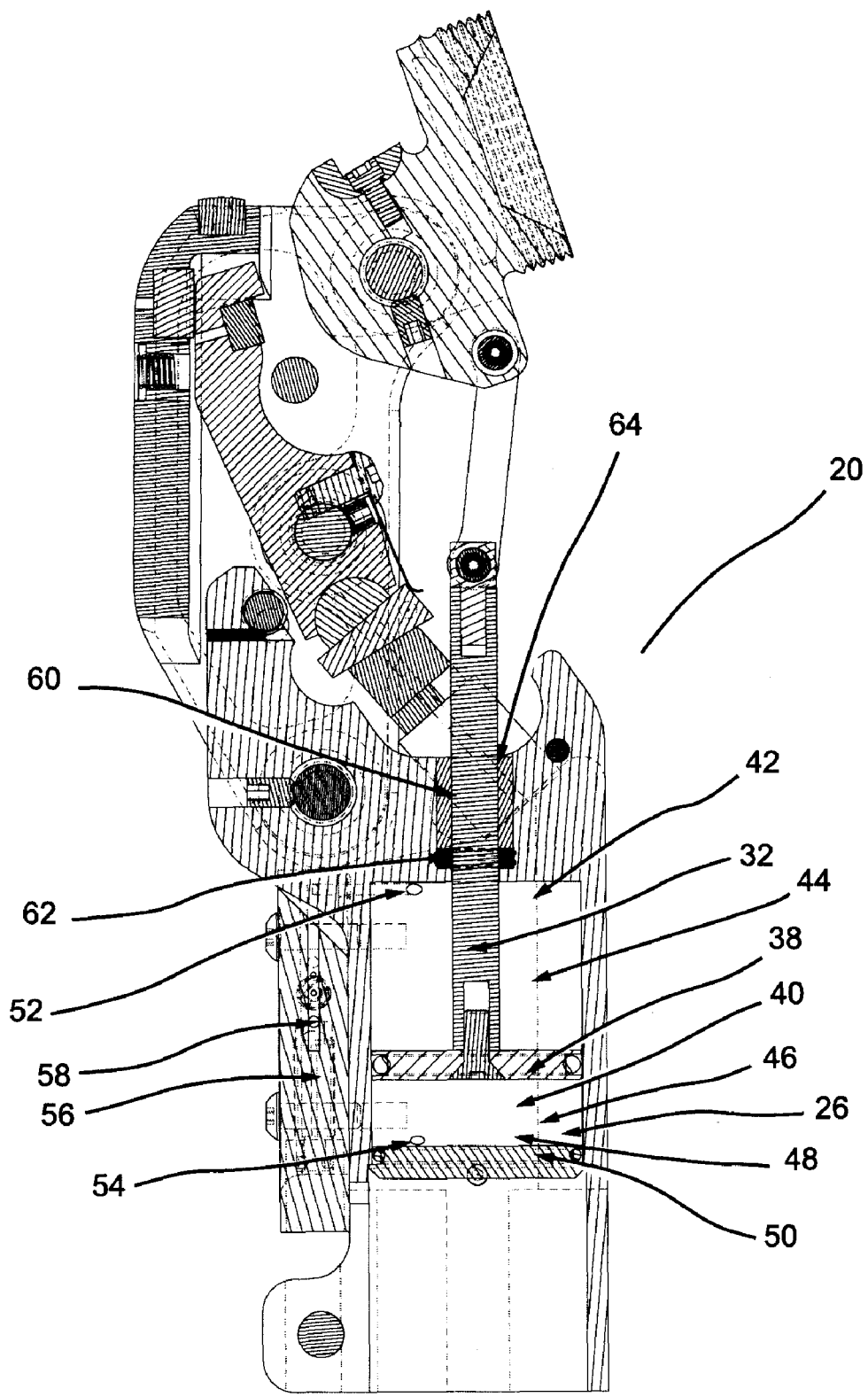
FIG. 4 in a partially sectioned view, illustrates the artificial joint of FIG. 2.

Referring to FIGS. 3 and 4 the piston and cylinder assembly 20 further includes a piston rod 32 having a first end 34 that is adapted to engage the piston linkage assembly 30 and a second end 36 adapted to engage a piston 38. The second end 26 of the piston and cylinder assembly 20 has a cylinder bore 40 adapted to receive the piston 38 for dividing the cylinder bore 40 into first and second chambers 44 and 46 respectively. The second end 26 of the piston and cylinder assembly 20 may be positioned within the lower coupling element 28. The cylinder bore 40 has a second end 48 that accommodates a cylinder cap 50. The cylinder bore 40 also has a first orifice 52 in the first chamber 44 and a second orifice 54 in the second chamber 46. The cylinder bore 40 has a first end 42 that has a concentrically positioned small bore 64. A bearing 60 and seal 62 are fitted within the small bore 64 through which the piston rod 32 moves. The bearing 60 may be further defined as an axially long bearing for linearly constraining the piston rod 32. The bearing 60 positioned at the first end 42 of the cylinder bore 40, linearly contains the piston rod 32 thereby providing support to the piston linkage assembly 30 when side loads or non-axial loads are placed on the piston linkage assembly 30.

The positioning of the piston linkage assembly 30 also allows for the piston linkage assembly 30 to accommodate flexing angles of 150°, for example when the artificial joint 10 is in a kneeling or sitting position (FIG. 5c). This degree of flexion is not as frequent as the typical degree of flexion for walking, which does not generally exceed 65°. Furthermore as the frequency and the velocities exhibited during kneeling and sitting are low, the wear on the artificial joint 10 is minimal.

The piston and cylinder assembly 20 further comprises a manifold 56 having a series of valves and channels 58 which allow for communication between the first and second chambers, 44 and 46 via the first and second orifices 52 and 54. The manifold 56 may be mounted to the cylinder bore 40 within the lower coupling element 28. The piston cylinder assembly 20 may either be hydraulic or pneumatic.

Figure 10C:
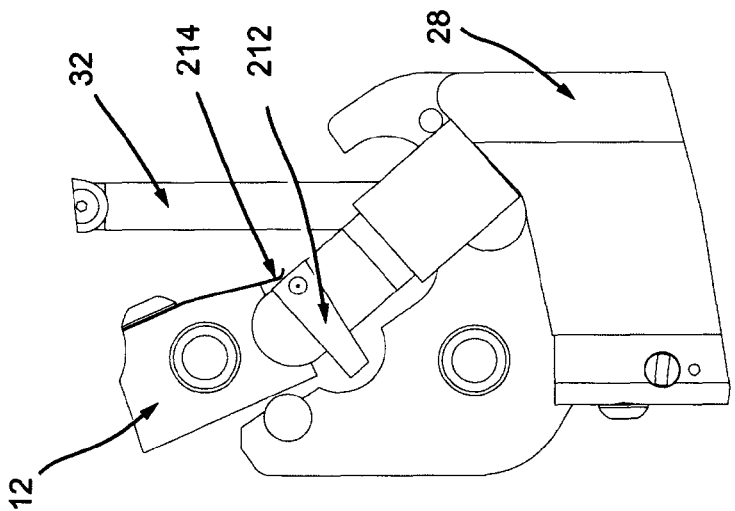
FIG. 10a in a side view, illustrates a prior art artificial joint.
FIGS. 10b and c in side views, illustrate the artificial joint of FIG. 1 and the activation of the biased compensation element.
Figure 10B:
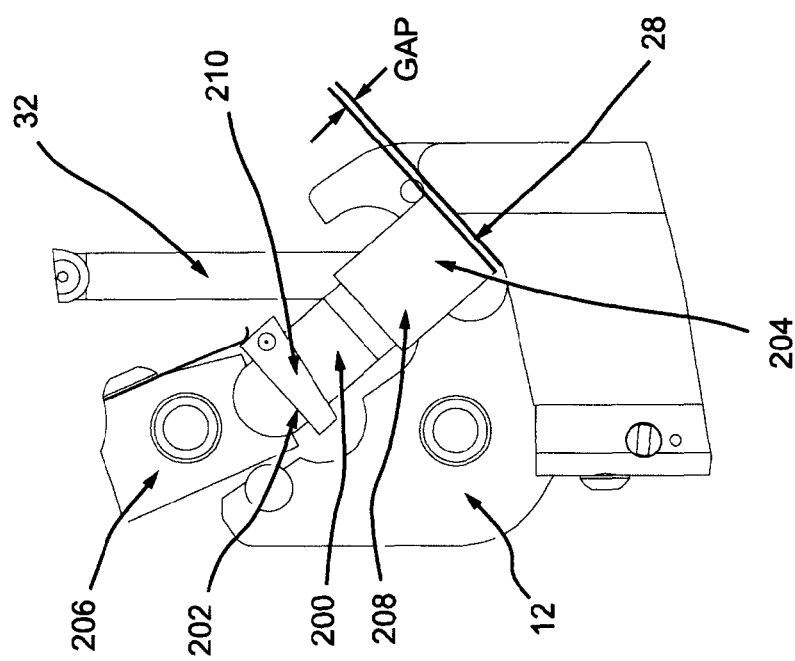

Referring to FIGS. 10b and c the stance-phase control means 12 is further defined as having an adjustable force transfer linkage assembly 200 having a first end 202 adapted to engage a latching or locking mechanism 206 and a second end 204 adapted to engage the lower coupling element 28. The second end 204 of the adjustable force transfer linkage assembly 200 is further defined as an elastomeric portion 208 configured to be positioned on either side of the piston rod 32, so that the piston rod 32 can move freely during the operation of the artificial joint 10, yet the elastomeric portion 208 may sit flat against the lower coupling element 28. The first end 202 of the adjustable transfer linkage assembly 200 is a biased compensation element 210 adapted to engage the latching mechanism 206. The biased compensation element 210 may be a wedge 212 that is positioned or activated by a spring 214 for example.

Figure 10A:
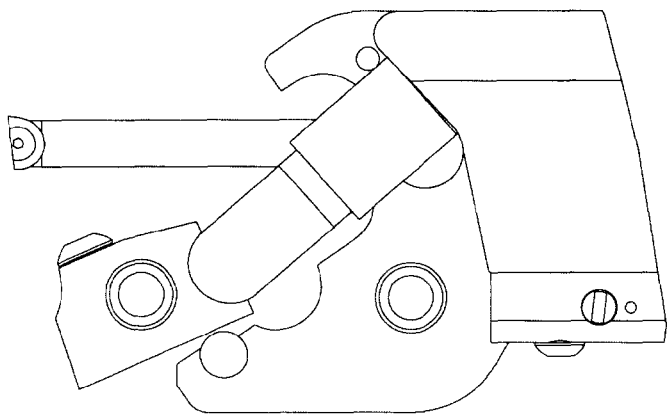

FIG. 10a illustrates prior art artificial joints that do not include a biased compensation element which produces a gap at the lower coupling element 28 and a wobble in the joint. FIGS. 10b and c illustrate the wedge 212 positioned by the spring 214 thereby changing the length of the force transfer linkage assembly 200. The spring 214 therefore ensures that the wedge 212 fits snugly between the lower coupling element 28 and the latching mechanism 206. The positioning of the wedge 212 during loading of the artificial joint 10, when the artificial joint 10 is locked, helps to decrease a wobbly effect caused by unresisted flexion/extension about the control axis 16. Specifically the wedge 212 compensates for changes in tolerance in the artificial joint 10 due to manufacturing or wear. This compensation results in an improved gait and more natural gait during the swing and stance-phases when the artificial joint 10 is incorporated into a knee joint for example.

Figure 6:
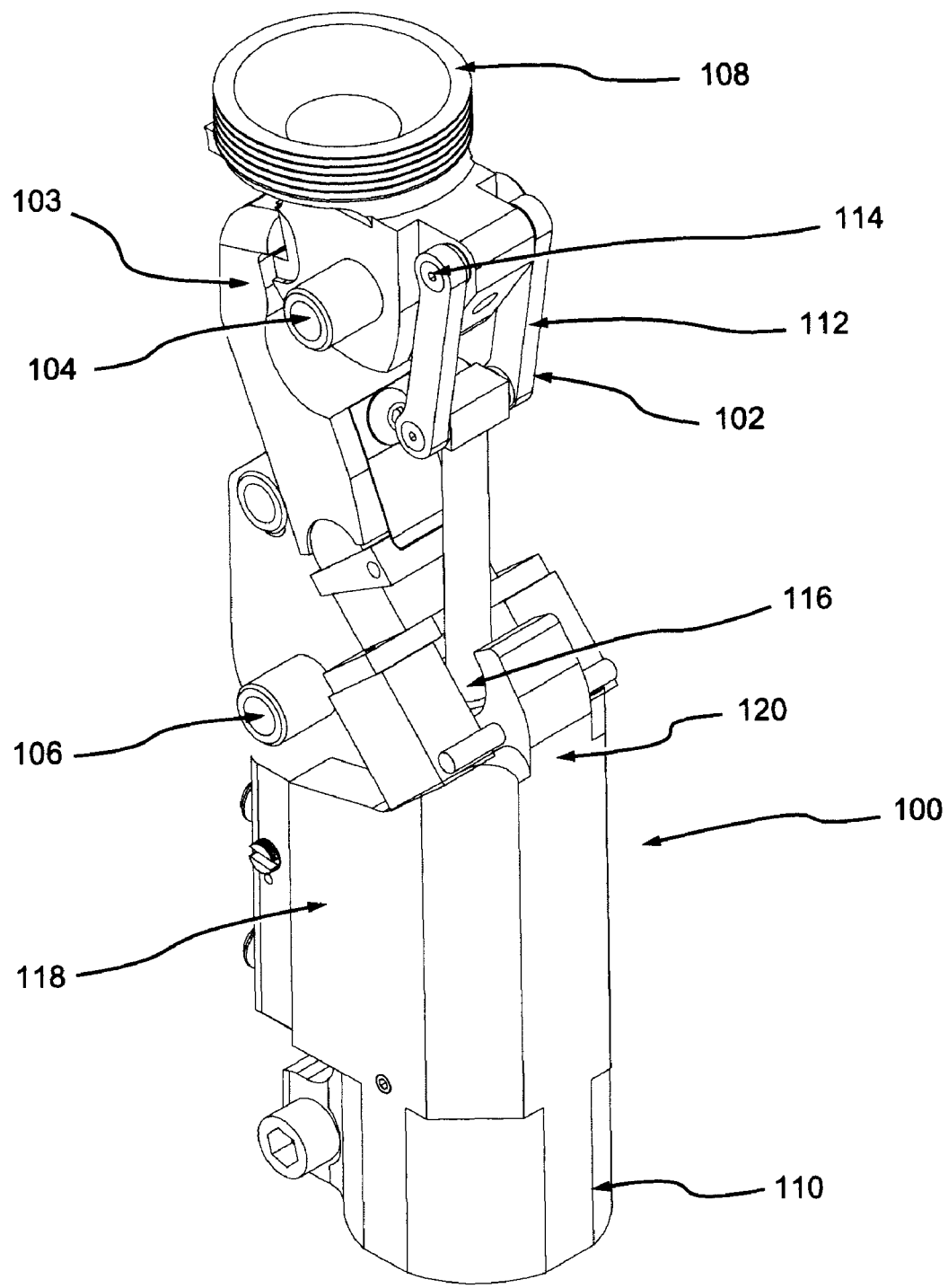
FIG. 6 in a perspective view, illustrates the swing-phase controller in accordance with another preferred embodiment of the present invention.
Figure 7:
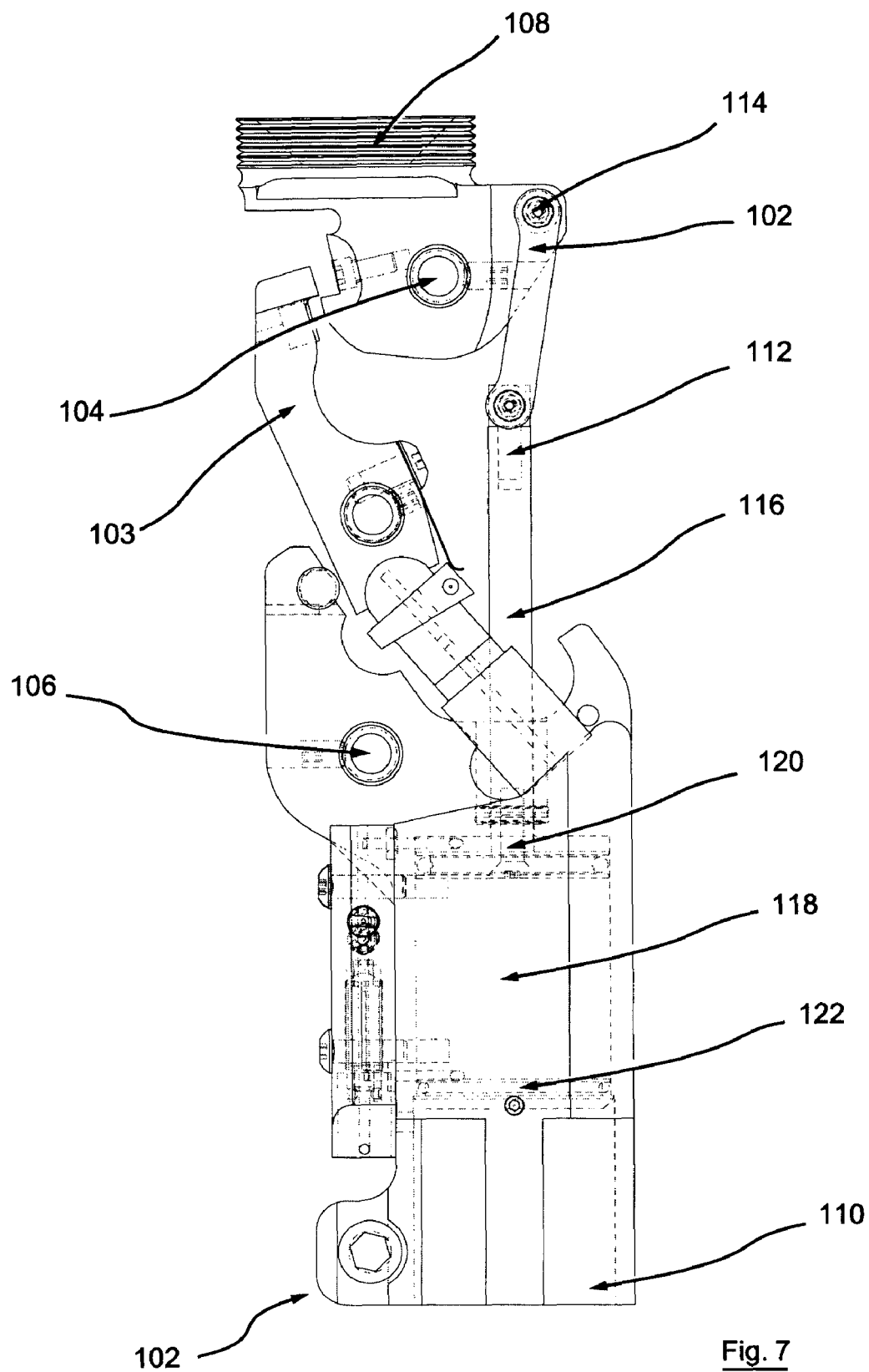
FIG. 7 in a side view, illustrates the artificial joint of FIG. 6.

Referring to FIGS. 6 and 7 in perspective and side views there is illustrated a swing-phase controller 100 for an artificial joint 102 in accordance with another preferred embodiment of the present invention. The swing-phase controller 100 for an artificial joint 102 having a stance-phase control means 103 with a flexing axis 104, a control axis 106, an upper coupling element 108, and a lower coupling element 110, where the swing-phase controller 100 has a piston assembly 112 having a first end 114 and a second end 116. The first end 114 is adapted to engage the upper coupling element 108 wherein the perpendicular distance from the piston assembly 112 to the flexing axis 104 and the perpendicular distance from the piston assembly 112 and the control axis 106 are relatively equal when the artificial joint 102 articulates about the flexing axis 104 up to 65°. The swing-phase controller 100 further includes a cylinder assembly 118 having a first end 120 and a second end 122, the second end 122 is adapted to engage the lower coupling element 110 so that the second end 116 of the of the piston assembly 116 is adapted to engage the first end 120 of the cylinder assembly 118.

Figure 8:
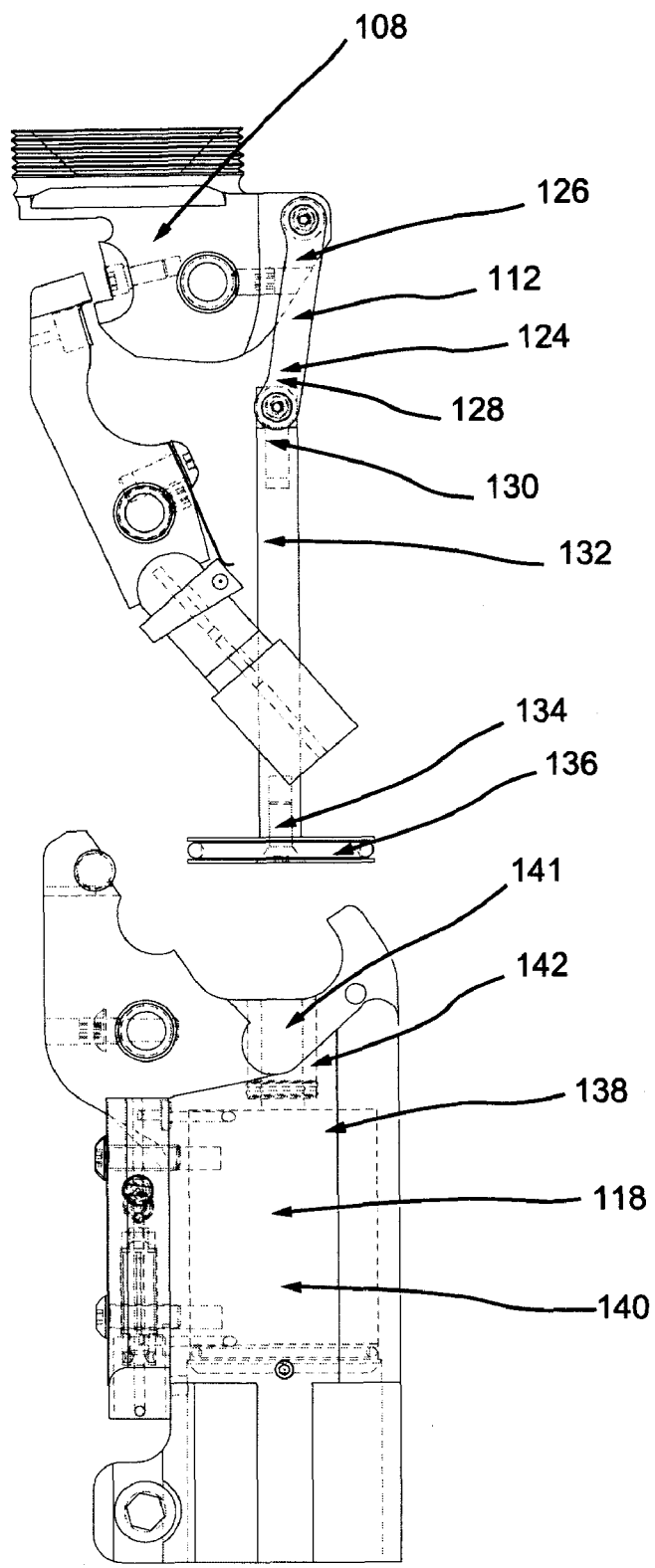
FIG. 8 in an exploded view, illustrates the artificial joint of FIG. 6.
Figure 9:
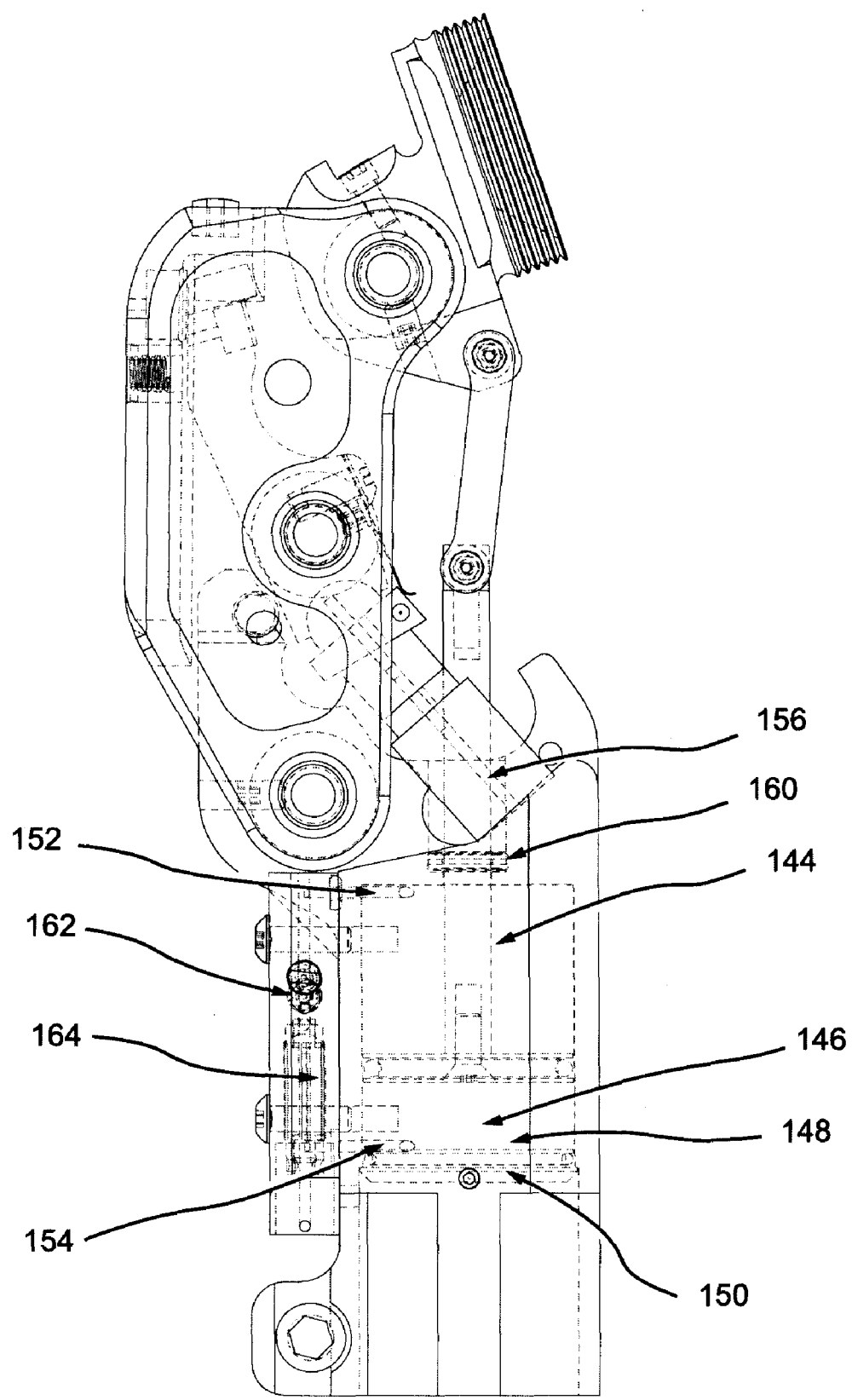
FIG. 9 in a partially sectioned view, illustrates the artificial joint of FIG. 7.

Referring to FIGS. 8 and 9 the piston assembly 112 has a piston linkage 124 having a first end 126 adapted to engage the upper coupling element 108, and a second end 128 adapted to engage a first end 130 of a piston rod 132, the piston rod 132 having a second end 134 with a piston 136. The cylinder assembly 118 has a wall 138 surrounding a defined cylinder bore 140 having a first end 142 adapted to receive the piston 136 for dividing the cylinder bore 140 into first and second chambers 144 and 146 respectively, and a second end 148 having a cylinder cap 150. The cylinder assembly 118 has a first orifice 152 through the wall 138 in the first chamber 144 and a second orifice 154 through the wall 138 in the second chamber 146. The first end 142 of the cylinder bore 140 further includes a concentrically positioned small bore 141 and further includes a bearing 156 and a seal 160 through which the piston rod 132 moves.

The cylinder assembly 118 further includes a manifold 162 having a series of valves and channels 164 which allows for communication between the first and second chambers 144 and 146 respectively via the first and second orifices 152 and 154. Both the piston and cylinder assemblies 112 and 118 may be either hydraulic or pneumatic.

The artificial joint 10 may be used in a variety of applications for example as a prosthetic, orthotic or robotic joint. The following describes the artificial joint 10 in operation in a prosthetic knee joint. In operation the knee joint should be controlled so that during weight bearing, the knee latching or locking mechanism 206 is inactive when the fore foot is loaded, or similarly, the knee lock is activated only when the rear and/or mid-region of the foot is loaded. During operation, the knee joint would normally collapse as the load line passes behind the flexing axis or knee axis 14 and causes a flexion moment at the knee axis 14. However, in the instant invention the inclusion of the control axis 16 provides the control, such that as long as there is a flexion moment at control axis 16, a locking mechanism 206 can be activated at knee axis 14. The user can therefore roll over the foot until the toe is loaded, at which point the person will apply a flexion moment at the hip via their muscles. The application of the flexion moment will cause the load line to pass posterior of the knee axis 14, but still be anterior of the control axis 16, therefore causing an extension moment about control axis 16 and thereby deactivating the locking mechanism 206. Therefore the knee joint is able to bend and the swing-phase can be initiated.

Control of the articulation of a knee during the swing-phase is controlled by the swing-phase control means 18. The main purpose is to provide appropriate levels of resistance at the flexing or knee axis 14. By providing appropriate levels of resistance during the flexing movement there is improved timing of the swing-phase, lessened excessive heels rise during mid-swing-phase and decreased the terminal impact as the leg straightens out at the end of swing-phase. The inclusion of the swing-phase control means 18 makes the gait more efficient and more natural looking and reduces wear between the locking mechanism 206 and the upper coupling element 24.

The stance-phase control means 12 however, controls how the artificial knee joint locks, as well as how the latching or locking mechanism 206 is controlled. In general the locking of the artificial knee joint 10 may generally include the locking mechanism 206 such as a latch, plunger or lock. The acting torque or moment at the control axis 16 determines whether the latch or lock is engaged or disengaged and is a function of the loading of the prosthesis.

More specifically a flexion moment will cause lock engagement and an extension moment will cause lock disengagement. For example if the artificial joint 10 does not have a swing-phase control means 18, and the leg is swinging, no internal moment is generated at the flexing or knee axis 14. There is also essentially no internal moment generated at the control axis 16. With the inclusion of the swing-phase control means 18, a moment at the flexing or knee axis 14 is generated so as to provide the swing-phase control. The generation of this moment however, results in the generation of a second moment, slightly smaller in magnitude, about the control axis 16. It is this moment that can have potentially adverse effects on the engagement and disengagement of the stance-phase control means 12 and especially adverse effects on the wear of the locking mechanism 206. Specifically the sliding contact between the locking mechanism 206 or latch and upper coupling element 24 will result in wear of these mechanisms. If the force of contact can be reduced by disengaging the lock (i.e. an extension moment at the control axis 16) then the wear will be reduced on the locking mechanism 206 or latch and upper coupling member 24.

In operation, as resistance is applied at the flexing or knee axis 14 with the implementation of a swing-phase control means 18, the moment generated about the control axis 16 will cause the engagement or activation of stance-phase control means 12, namely the locking mechanism 206, thereby increasing wear between the locking mechanism 206 and the upper coupling element 24. The moment at the control axis 16 however is eliminated or does not adversely affect the locking mechanism 206 and the upper coupling element 24 when the perpendicular offset or distance of the piston linkage assembly 30 from the flexing or knee axis 14 $d_{KA}$ and control axis 16 $d_{CA}$ are relatively equal.

Referring to Table 1, the percentages of difference between $d_{KA}$ and $d_{CA}$ offsets through angles 0 to 65° are set out. The differences between $d_{KA}$ and $d_{CA}$ offsets can vary from 0% to as much as 70% during knee flexion. Despite the sometimes large percentage of difference at various points during the knee flexion, the relationship between the swing-phase control means 18 and the control axis 16 and the flexing axis 14, as set out in the description above, still limits wear and preserves the stance-phase function. However, for knee flexion specifically at 65°, which represents the flexion angle during walking, the offsets often remain relatively equal.

TABLE 1

| Knee Angle (degrees) | dKA (mm) | dCA (mm) | difference(%) |
|---|---|---|---|
| 0 | 13.24 | 13.24 | 0 |
| 10 | 14.59 | 11.07 | 32 |
| 20 | 15.81 | 10.03 | 58 |
| 30 | 16.79 | 10.04 | 67 |
| 40 | 17.38 | 11 | 58 |
| 50 | 17.37 | 12.69 | 37 |
| 60 | 16.6 | 14.87 | 12 |
| 65 | 15.88 | 16.06 | −1 |

Furthermore FIGS. 5a-c illustrate that the $d_{KA}$ and $d_{CA}$ offsets are not always constant as a function of knee flexion/extension. The following describes the interaction within the artificial joint at various points of flexion and that relationship to the $d_{KA}$ and $d_{CA}$ offsets:

During Knee Flexion:

Between 0-65°, the $d_{KA}$ offset is greater than the $d_{CA}$ offset resulting in the engagement of the locking mechanism 206 in the artificial joint 10. Normally there would be increased wear on the locking mechanism 206, however, during this range of the swing-phase, there is minimal resistance so the wear on the artificial joint 10 is minimal. Furthermore when the artificial joint 10 utilizes a pneumatic cylinder, for 0-50° of flexion, the resistance to flexion is minimal as the air is becoming compressed. However once the air becomes compressed, the air provides greater resistance. This increased resistance is desired at higher flexion angles to limit the amount of heel-rise. At higher flexion angles, such as between 50-65°, the air in the pneumatic cylinder is compressed and provides a high level of resistance to limit heel-rise. At this juncture the $d_{KA}$ offset and $d_{CA}$ offset are essentially equal and the locking mechanism 206 will disengage therefore eliminating wear.

During Knee Extension:

During the majority of the return of the leg to the extension position, namely between 65-0°, the $d_{KA}$ offset is greater than the $d_{CA}$ offset, which results in the internal extension moment to be generated at the control axis 16. The creation of this moment eliminates wear in the artificial joint 10 as the locking mechanism 206 disengages as discussed above. At full extension, the $d_{KA}$ and $d_{CA}$ offsets are essentially equal and this ensures that approximately no moment is generated at the control axis 16 and the locking mechanism 206 will engage as is appropriate.

Where the artificial joint 10 utilizes a hydraulic cylinder, there is usually low resistance during initial knee flexion, then increased resistance at later knee flexion to limit heel-rise, then low resistance during extension until just prior to full knee extension, and finally increased resistance to decelerate the leg and limit terminal impact at full knee extension. The hydraulic cylinder therefore functions in a similar manner to the pneumatic cylinder described above, and therefore provides improved function with the stance-phase control means.

Figures 11A, 11B:
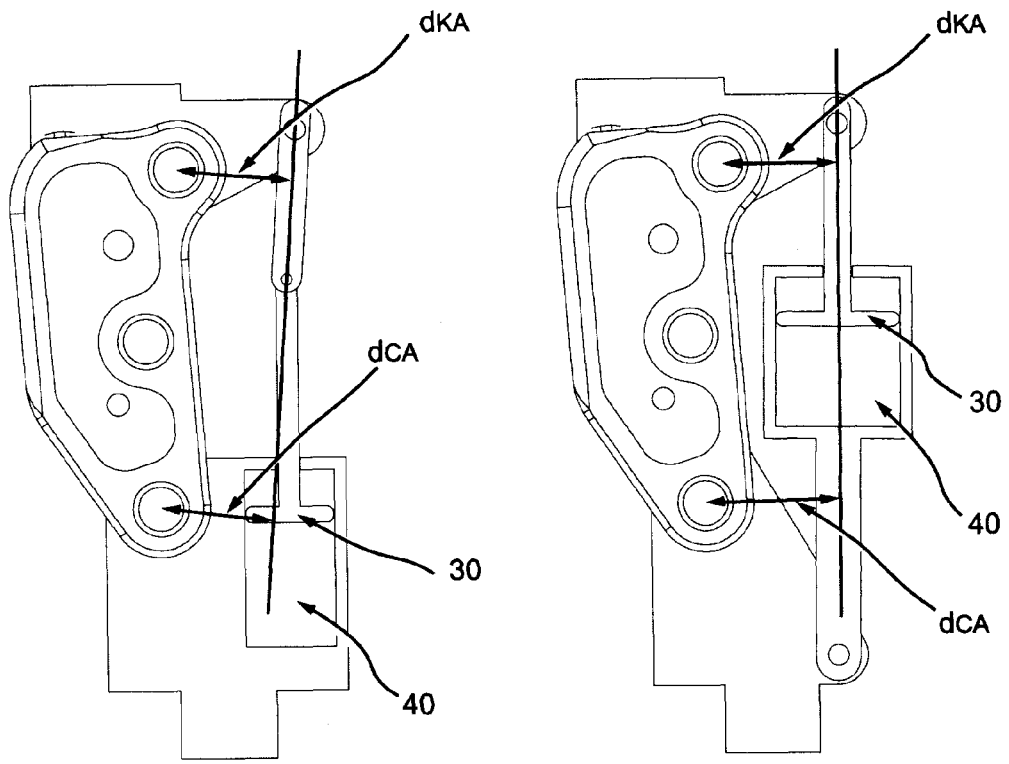
FIGS. 11a and b in side views, illustrate the swing-phase controller relative to the control axis and knee axis in another preferred embodiment of the present invention.
Figures 11C, 11D:
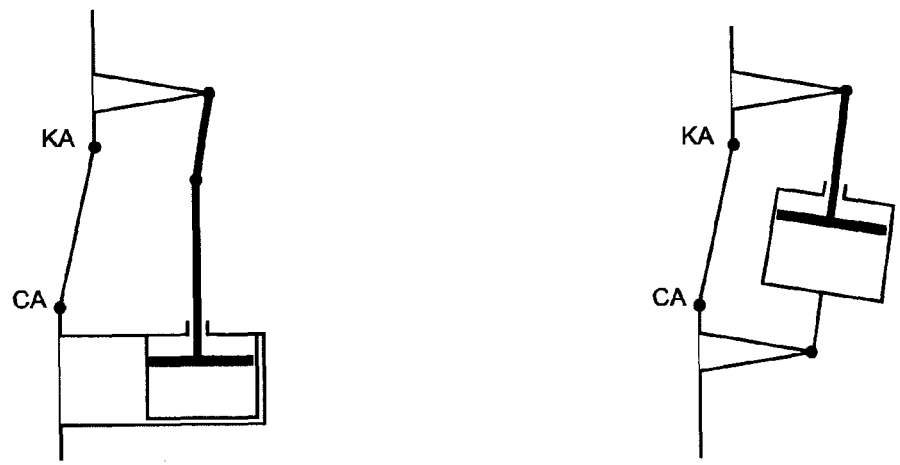
FIGS. 11c, and d in schematic views, illustrate the offset distances from the piston linkages to the knee axis and control axis.

FIGS. 11a and b illustrate that the offset distances from the piston linkage assembly 30 and the cylinder bore 40 are relatively equal to one another when the artificial joint 10 articulates up to 65°. Furthermore FIGS. 11a-d show the different positioning of the piston cylinder assemblies 20 relative the stance-phase control means 12.

Table 2 describes the relationship between offset distances and effect on lock/stance-phase controller function. It is generally true that during flexion a passive flexion resisting moment (or extension moment) is generated (i.e. the passive moment is always in the opposite direction). So if the knee is tending to flex, the moment is resisting flexion and therefore is acting in the opposite, extension direction. This works well for truly passive devices like a hydraulic cylinder. However, for a pneumatic cylinder, which acts in part like a spring as the air compresses, the moment may not always be opposite to the direction of motion. During heel-rise the leg is flexing it is being decelerated by a combination of damping moments caused by the flow of air and also the spring like force of the compressed air. The leg finally stops and then begins to extend. The damping moment reverses direction, but the spring moment still acts in the same direction. If this spring moment is in excess of the passive damping moment, the swing-phase controller will actually be acting to accelerate the leg. Therefore an extension moment will be applied to the extending leg for a short amount of time.

TABLE 2

| | Internal extension moment at KA is generated (Generally occurs during knee flexion) | Internal flexion moment at KA is generated (Generally occurs during knee extension) |
|---|---|---|
| If $d_{KA} \ll d_{CA}$ | Lock is tending to disengage - wear is decreased at latch | Lock is tending to engage - wear is increased but knee will securely at the end of swing-phase |
| If $d_{KA} \gg d_{CA}$ | Lock is tending to engage - wear is increased at latch | Lock is tending to disengage - wear is decreased at latch but knee may not lock at the end of swing-phase |

In operation the piston linkage assembly 30 of the swing-phase control means 18 transmits motion or forces from the upper coupling element 24 through the piston rod 32 and to the piston 38. The piston rod 32 slides through first end 42 of the cylinder bore 40 through the bearing 60 and a dynamic seal 62 located in the small bore 64. The piston 38, which can incorporate a dynamic seal, separates the space within the cylinder bore 40 into the first and second chambers, 44 and 46, or the upper and lower chambers. When the piston rod 32 is moved, the first and second orifices 52 and 54 in each of the chambers 44 and 46, and the network of channels and valves 58 found in a manifold 56, allow for the flow of fluid (air or oil) from one chamber to the other to be controlled. Flow restrictions in the manifold 56 can be provided by valves 58 to resist the motion of the piston 38 and therefore the flexion and extension of the knee. When the knee is being flexed, resistance to flexion results from fluid in the lower chamber 46 being forced into the upper chamber 44. By changing the ease of flow, the resistance of knee flexion is altered. The same pertains to knee extension.

Other variations and modifications of the invention are possible. All such modifications or variations are believed to be within the sphere and scope of the invention as defined by the claims appended hereto.

I claim:

1. An artificial joint comprising:
    (a) a stance-phase control system having a flexing axis, a control axis and upper and lower coupling elements, and a lock, wherein the lock engages or disengages with a flexing or an extension moment, respectively, generated about the control axis; and
    (b) a swing-phase control system comprising: a piston and cylinder assembly and linkage assembly, wherein the upper and lower coupling elements are each linked to a portion of the swing-phase control system such that the piston and cylinder assembly generates a resistance force against flexing,
    wherein a load line of the resistance force passing through an uppermost link of the linkage assembly to the upper coupling element defines a longitudinal axis, such that:
    (1) the shortest distance between the flexing axis and the longitudinal axis, and
    (2) the shortest distance between the control axis and the longitudinal axis are substantially equal when the artificial joint articulates about the flexing axis to an angle to disengage the lock so as to reduce a moment, about the control axis, generated by the swing-phase control system.

2. An artificial joint as claimed in claim 1 wherein the piston and cylinder assembly further comprises a piston rod having a first end adapted to engage the linkage assembly and a second end adapted to engage a piston.

3. An artificial joint as claimed in claim 2 wherein the second end of the piston and cylinder assembly has a cylinder bore having a first end adapted to receive the piston for dividing the cylinder bore into first and second chambers.

4. An artificial joint as claimed in claim 3 wherein the cylinder bore has a second end having a cylinder cap and a first orifice in the first chamber and a second orifice in the second chamber.

5. An artificial joint as claimed in claim 4 wherein the piston and cylinder assembly further comprises a manifold having a series of valves and channels allowing for communication between the first and second chambers via the first and second orifices.

6. An artificial joint as claimed in claim 1 wherein the stance-phase control system further comprises an adjustable force transfer linkage assembly having a first end with a biased compensation element adapted to engage the lock, and a second end having an elastomeric portion adapted to engage the lower coupling element wherein the activation of the biased compensation element adjusts the length of the adjustable force transfer linkage assembly.

7. An artificial joint as claimed in claim 1 wherein the piston and cylinder assembly is hydraulic or pneumatic.

8. An artificial joint as claimed in claim 1, wherein the angle is approximately 65°.

* * * * *